United States Patent [19]
Alvine

[11] Patent Number: 5,326,365
[45] Date of Patent: Jul. 5, 1994

[54] ANKLE IMPLANT

[76] Inventor: Franklin G. Alvine, 405 Harpel Dr., Sioux Falls, S. Dak. 57105

[21] Appl. No.: 867,151

[22] Filed: Apr. 10, 1992

[51] Int. Cl.5 .............................................. A61F 2/42
[52] U.S. Cl. ..................................................... 623/21
[58] Field of Search .................................... 623/18, 21

[56] References Cited

U.S. PATENT DOCUMENTS

| | | | |
|---|---|---|---|
| 4,069,518 | 1/1978 | Groth, Jr. et al. | 623/21 |
| 4,156,296 | 5/1979 | Johnson et al. | 623/21 |
| 4,193,139 | 3/1980 | Walker | 623/21 |
| 4,194,250 | 3/1980 | Walker | 623/21 |
| 4,232,404 | 11/1980 | Samuelson et al. | 623/21 |
| 4,755,185 | 7/1988 | Tarr | 623/21 X |
| 5,080,679 | 1/1992 | Pratt et al. | 623/18 X |

OTHER PUBLICATIONS

"Irvine Ankle Arthroplasty", Waugh et al., *Clinical Orthopaedics and Related Research*, No. 114, pp. 180–184, Jan.–Feb. 1976.
"Evaluation of the Early Result of Smith Total Ankle Replacement", Dini et al., *Clinical Orthopaedics and Related Research*, No. 146, pp. 228–230, Jan.–Feb. 1980.
"Total Ankle Arthroplasty: Four Years' Experience", Stauffer et al., *Clinical Orthopaedics and Related Research*, No. 160, pp. 217–221, Oct. 1981.
"Total Ankle Replacement in Rheumatoid Arthirits", Lachiewicz et al., *The Journal of Bone and Joint Surgery*, vol. 66-A, No. 3, pp. 340–343, Mar. 1984.
"Total Ankle Arthroplasty", Bolton-Maggs et al., *The Journal of Bone and Joint Surgery*, vol. 67-B, No. 5, pp. 785–790, Nov. 1985.
"Long-term Results of Total Ankle Replacement", Helm et al., *The Journal of Arthroplasty*, vol. 1, No. 4, pp. 271–277, Dec. 1986.
"Total Ankle Arthroplasty in Rheumatoid Arthritis: A Long-term Follow-up Study", Unger et al., *Foot & Ankle*, vol. 8, No. 4, pp. 173–179, Feb. 1988.
"New Jersey Low Contact Stress Total Ankle Replacement: Biomechanical Rationale and Review of 23 Cementless Cases", Buechel et al., *Foot & Ankle*, vol. 8, No. 6, pp. 279–290, Jun. 1988.
Exhibit "A" is series of drawings of an orthopedic ankle of Franklin Alvine.

*Primary Examiner*—Randall L. Green
*Assistant Examiner*—Mary Beth Jones
*Attorney, Agent, or Firm*—Merchant, Gould, Smith, Edell, Welter & Schmidt

[57] ABSTRACT

A replacement ankle joint includes a tibial member and a talar member. The tibial member has a bearing forming a concave surface which engages a curving dome surface of the talar member. The tibial member and talar member slide along the curved surfaces relative to one another to provide flexion and extension. The dome has tapering side walls which are complementary to side portions of the tibial bearing. The tibial member includes a wide base plate proximate the bearing which attaches to the tibia and fibula.

17 Claims, 3 Drawing Sheets

ANKLE IMPLANT

BACKGROUND OF THE INVENTION

1. Field of the Invention

The present invention relates to a replacement ankle which is permanently implanted.

2. Description of the Prior Art

Prosthetic devices which are implanted for replacement of joints are well known. Such implants take the place of the body's own joints which fail, such as may be required for patients suffering from rheumatism, degenerative or traumatic arthritis. A number of problems are associated with joint replacement. The joint should function in a manner which simulates the natural joint, providing substantially the same degree of motion. In particular, for ankle replacements, the joint should supply at least the same degree of motion as is required for walking. In addition, the joint should not occupy more space in the body than the natural joint. Problems also arise in connecting the replacement joint to bone and tissue. The joint should also be as easy to implant as possible without the use of surgical cement, so that intricate operations are not required, reducing the chances of complications. The Joint must have sufficient strength and durability to withstand the weight and stresses which are applied.

Ankle joints pose additional problems due to the weight supported and the range of motion required for walking. Attachment of the tibia which extends substantially vertically is difficult, as portions of the fibula may also be removed for implants. Matching the pivot point of the joint is critical, as misalignment may lead to difficulty in walking and other motions, which may cause the patient considerable pain. The durability of a replacement joint is also important, as the ankle experiences high stresses during walking, running, and jumping as well as fatigue over time. These stresses may crack or fracture ankle components of replacement joints, which absorb a substantial amount of the pressures during the aforementioned activities.

It can be seen then that a replacement ankle is needed which is inexpensive and easily implantable while providing sufficient range of motion which approaches that of a natural ankle Joint. It can also be seen that the utility of such an ankle is increased if the ankle occupies a space comparable to that of the natural ankle and is durable enough to withstand the stresses which are placed upon an ankle joint.

SUMMARY OF THE INVENTION

The present invention is directed to an ankle joint for implanting during ankle replacement surgery. According to the present invention, an ankle joint has a tibial member and a talar member which provide a range of motion comparable to that of a natural ankle.

The talar member has a dome portion with a semicircular arcing surface and tapering sides. The underside of the dome is flat with a strut extending therefrom which attaches to the bone.

The tibial member has a bearing holder and a tibial bearing which engages the domed portion of the talar member. The bearing has a concave surface that is complementary to the dome. The dome portion slides in the concave surface of the tibial bearing. The bearing has side portions extending down along both sides of the dome. The side portions are also tapered to prevent excessive lateral sliding while permitting limited rotation between the tibial member and the talar member.

The bearing holder includes an obliquely rectangular base plate which is sufficiently wide to bridge the tibia and the fibula. The base plate has a thickness that minimizes bone removal, yet has sufficient strength to withstand the stresses and fatigue it receives after implantation. The bearing holder has side walls extending from the base plate proximate the side portions of the tibial bearing, adding support to the bearing. A strut extends up from the base plate, to attach to the tibia for positioning the tibial member following implantation. The wide base plate provides for fusing of the tibia and fibula, thereby transferring some weight bearing to the fibula and broadening the bony base.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

In the drawings, wherein like reference numerals and letters indicate corresponding elements throughout the several views.

DETAILED DESCRIPTION OF THE PREFERRED EMBODIMENT(S)

Figure 1:
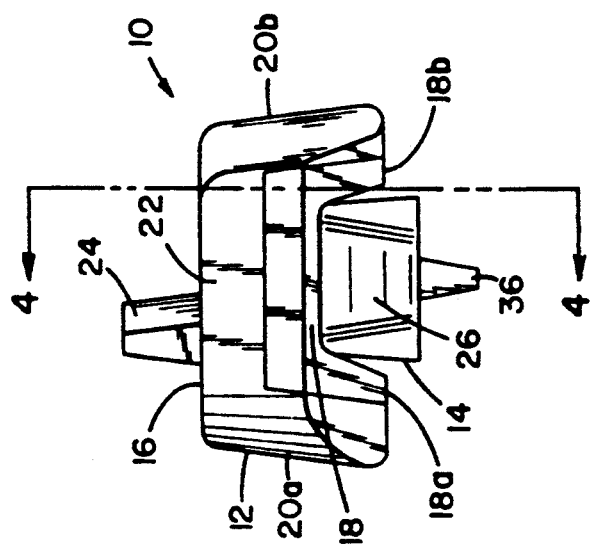
FIG. 1 shows a front elevational view of a prosthetic left ankle according to the principles of the present invention.

Referring now to the drawings and in particular to FIG. 1, there is shown an implantable ankle device, generally designated 10. A left ankle is shown, a right ankle being a mirror image of the left. The ankle 10 is configured for replacement surgery wherein the patient's ankle is replaced. The ankle device 10 has a tibial member 12 and a talar member 14 which interact to provide flexion and extension similar to that of a normal ankle. The implanted ankle 10 has a compact shape which requires minimal removal of the patient's bone and tissue.

The tibial member 12 has a tibial bearing 18 which fits into a bearing holder 16. The bearing holder has a base plate 22 and positioning walls 20, including a medial wall 20a and a lateral wall 20b, which extend from the base plate on both sides of the tibial bearing 18. A strut 24 extends upward from the tibial base plate 22 opposite the tibial bearing 18.

Figure 4:
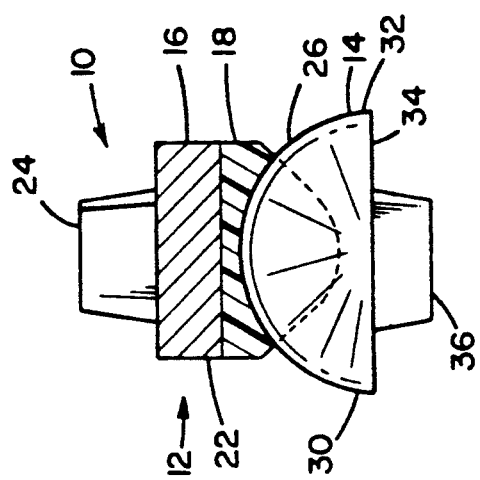
FIG. 4 shows a sectional view taken along line 4—4 of FIG. 1 with the ankle in a flexed position.

The talar member 14 has a tapering dome portion 26 which tapers along its arc. The dome portion 26 has a semicircular curving surface 28 with sides that angle slightly outward from a first anterior end 30 to a second posterior end 32 of the arc, as shown in FIG. 4. A flat underside 34 of the talar member 14 has a talar strut 36 which is configured for extending downward and attaches to the talus. The sides of the dome 26 also taper inward from the underside 34 radially outward to facilitate alignment and ease sliding of the members 12 and 14.

Figure 2:
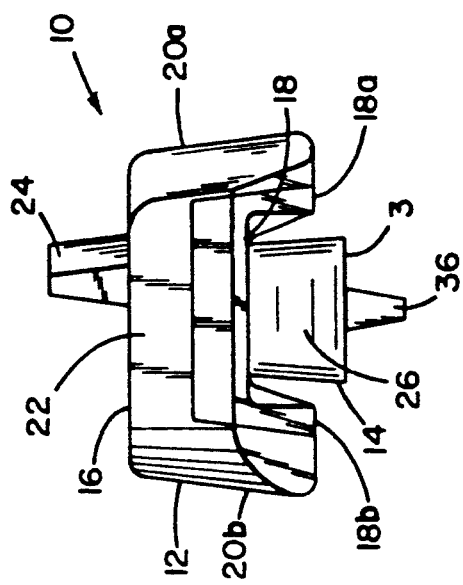
FIG. 2 shows a rear elevational view of the ankle shown in FIG. 1.
Figure 3:
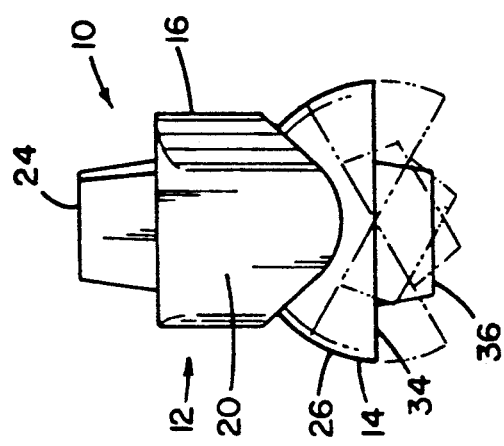
FIG. 3 shows a side elevational view of the ankle shown in FIG. 1 in an extended position.

As shown in FIG. 2, the tapering dome portion 26 of the talar member 14 fits in a complementary manner with the tibial bearing 18. The concave surface of the tibial bearing 18 fits against the dome portion 26. Side portions 18a and 18b of the tibial bearing proximate the positioning walls 20 engage the sides of the dome portion 26. The dome portion 26 slides and pivots relative to tibial bearing 18. It is important that the tibial bearing 18 provide a sliding surface that is compatible for implantation, yet will not wear. In the preferred embodiment, the tibial bearing 18 is made of a durable polyethylene while the bearing holder 16 is made of titanium and the talar member 14 is made from a cobalt chrome alloy, however, other materials exhibiting the same characteristics may be utilized. The tibial bearing 18 and the dome portion 26 provide for a range of motion of approximately sixty degrees between an extended position and a flexed position, as shown in FIG. 3.

Figure 5:
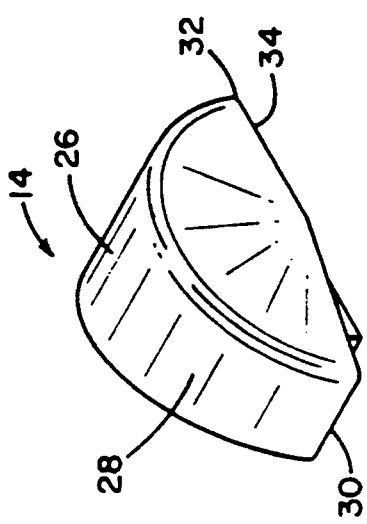
FIG. 5 shows a perspective view of the talar member.

Referring again to FIG. 1, it can be seen that the side portions 18a and 18b and the positioning walls 20a and 20b retain the talar member 14 from lateral sliding at all positions. The walls 20 provide support to the joint so that the ankle joint 10 remains properly positioned at all times. As best shown in FIG. 5, the dome portion 26 widens slightly from anterior to posterior. The distance between the side portions 18a and 18b also widens in a similar manner, which keeps the members 12 and 14 aligned but also provides clearance between sides of the dome portion 26 and the side portions 18a and 18b to allow turning of the joint to either side while restricting the lateral rotation within a range comparable to that of a natural ankle joint.

The ankle 10 pivots at the meeting of the dome portion 26 and the tibial bearing 18. The surfaces slide relative to one another and allows pivoting to occur along a slightly moving pivot point, thereby having a motion and range of motion similar to that of a natural ankle joint.

Figure 8:
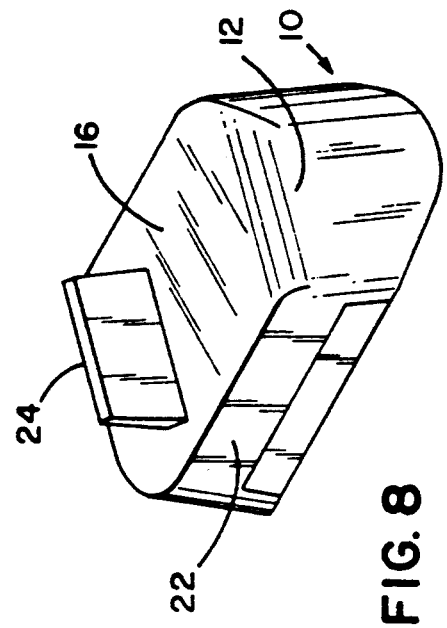
FIG. 8 shows a top perspective view of the tibial base plate.
Figure 6:
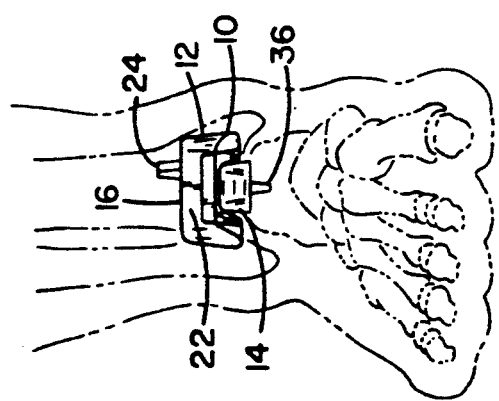
FIG. 6 shows a front elevational view of a right ankle joint implanted.

The base plate 22 of the tibial member 12 must be wide enough to bridge the area between the tibia and the fibula. As shown in FIG. 8, the tibial base plate 22 has an obliquely rectangular configuration wide enough to bridge the tibia and fibula. When implanted, the lateral wall 20b butts up against the fibula while the medial wall 20a butts against the medial malleolus, as shown in FIG. 6. In this manner, the fibula fuses to the tibia and a portion of the weight bearing is transferred to the fibula. The base plate 22 should be as thin as possible to minimize bone removal for implantation while maintaining sufficient strength to withstand the stresses which it faces. In the preferred embodiment, the tibial base plate 22 has a thickness of 0.130 inches. This thickness is sufficient to eliminate cracking and fatigue problems which occur with thinner base plates while keeping bone removal within acceptable limits. An increase in thickness of 0.05 inches up to a total thickness of 0.130 inches has been found to increase the strength of the base plate 22 and the overall support to the replacement ankle 10 by 429 percent, thereby greatly increasing the life and durability of the replacement ankle 10.

Figure 7:
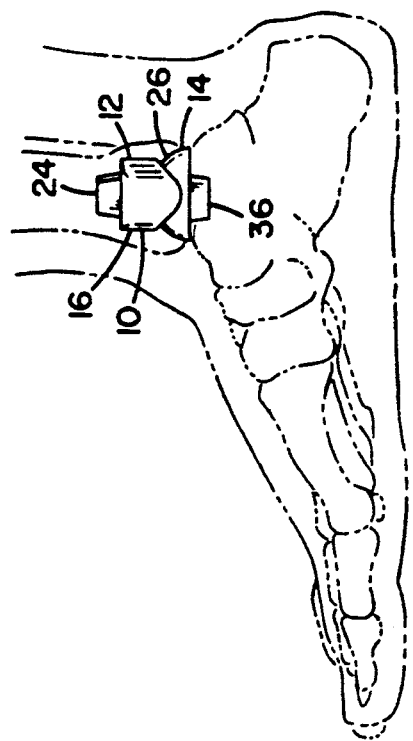
FIG. 7 shows a side elevational view of the ankle joint implanted.

As shown in FIGS. 6 and 7 the ankle 10 is implanted with the talar member 14 attaching to the talus and the tibial member 12 attaching to the tibia and fibula bones with the base plate 22 bridging the bones. The tibial strut 24 extends up into the tibia bone when implanted and also positions the tibial member 12 correctly. In a similar manner, the talar strut 36 extends down into the talus to keep the talar member 14 properly aligned when implanted. The ankle 10 is attached without cement as the surfaces of the ankle contacting the bones have a special coating, Porocoat TM, applied Using this surface treatment, microbeads of porous hot metal are blown onto the surface. As the metal cools, a lattice-like surface is created which facilitates attachment between the surface with bony ingrowth.

Since patients have different size ankles, different size ankle implants 10 are required. The correct size is obtained by comparing X-rays of each patient's ankle to an outline of each size implant. It has been found that small, medium and large size implants provide sufficient variation to accommodate virtually all ankle replacement situations.

It can be appreciated that the present invention provides a compact total ankle replacement with a range of motion comparable to that for a normal ankle. The ankle joint is compact, easy to implant, low cost and has minimal associated complications. The ankle is able to withstand the stresses and fatigue which cause failure in prior ankle devices.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A prosthetic ankle device, for ankle joint replacement, comprising:

a) a tibial member including a tibial bearing and a bearing holder, the tibial bearing having side portions and forming a concave surface intermediate the side portions, the bearing holder including a base plate proximate the bearing opposite the concave surface, and side walls laterally outside of the bearing side portions, the base plate including a tibial strut extending outward therefrom on a surface opposite the bearing; and, b) a talar member including a dome portion, the dome portion configured to mate with the concave surface of the tibial bearing, the dome extending along an arc from an anterior to a posterior position, wherein the dome includes sides tapering substantially along their entire length from the posterior to the anterior position, the talar member including a strut extending outward therefrom opposite the dome.

2. A prosthetic ankle device according to claim 1, wherein the thickness of the tibial base plate is 0.130 inches.

3. A prosthetic ankle device according to claim 1, wherein the talar member is made of a cobalt and chrome alloy and wherein the bearing holder is made of titanium.

4. A prosthetic ankle device according to claim 3, wherein the tibial bearing is made of polyethylene.

5. A prosthetic ankle device according to claim 1, wherein the side portions of the tibial bearing taper along their length from the posterior position to the anterior position complementary to the taper of the dome portion.

6. A prosthetic ankle device according to claim 5, wherein the concave surface of the tibial bearing curves so as to complement the dome portion.

7. A prosthetic ankle device according to claim 1, wherein the arc of the dome portion is a semicircle.

8. A prosthetic ankle device according to claim 1, wherein the ankle device provides a range of motion of sixty degrees between the tibial member and the talar member.

9. A prosthetic ankle joint, comprising:
a tibial joint member including a bearing, wherein the bearing forms a concave surface intermediate opposed side portions, the tibial joint member including a tibial base plate, proximate the bearing on a surface opposite the concave surface, wherein the tibial base plate has a thickness sufficient to withstand normal ankle joint fatigue and stresses;
a talar joint member, the talar member including a second engaging surface, wherein the second engaging surface comprises a tapering dome, the dome having sides tapering from a posterior position to an anterior position wherein the concave surface and second engaging surface coact so that the tibial member pivots relative to the talar member.

10. A prosthetic ankle joint according to claim 9, wherein the tibial base plate has a obliquely quadrilateral configuration and wherein the tibial base plate is adapted to bridge the tibia and fibula when implanted.

11. A prosthetic ankle joint according to claim 10, wherein tibial base plate is made of titanium and the talar member is made of a cobalt-chrome alloy.

12. A prosthetic ankle joint according to claim 11, wherein the tibial bearing is made of polyethylene.

13. A prosthetic ankle joint according to claim 10, wherein the tibial base plate is 0.130 inches thick.

14. A prosthetic ankle joint according to claim 10, further comprising a strut extending from the tibial base plate away from the bearing.

15. A prosthetic ankle joint according to claim 10, further comprising a strut extending from an underside surface of the dome portion.

16. A prosthetic ankle joint according to claim 9, wherein the side portions of the tibial bearing taper along their length from the posterior position to the anterior position complementary to the taper of the dome portion.

17. A prosthetic ankle device, for ankle joint replacement, comprising:
a) a tibial member including a tibial bearing and a bearing holder, the tibial bearing having side portions and forming a concave surface intermediate the side portions, the bearing holder including a base plate proximate the bearing opposite the concave surface, and side walls laterally outside of the bearing side portions, the base plate including a tibial strut extending outward therefrom on a surface opposite the bearing; and,
b) a talar member including a dome portion, the dome portion configured to mate with the concave surface of the tibial bearing, the dome extending along an arc from an anterior to a posterior position, wherein the dome includes sides tapering substantially along their entire length from the posterior to the anterior position, the talar member including a strut extending outward therefrom opposite the dome.

* * * * *